(12) United States Patent
Jeon et al.

(10) Patent No.: US 7,289,838 B2
(45) Date of Patent: Oct. 30, 2007

(54) APPARATUS AND METHOD FOR MEASURING BLOOD COMPONENTS

(75) Inventors: Kye-jin Jeon, Suwon-si (KR); In-duk Hwang, Suwon-si (KR); Eun-young Choe, Yongin-si (KR); Hye-jeong Kim, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 288 days.

(21) Appl. No.: 10/942,091

(22) Filed: Sep. 16, 2004

(65) Prior Publication Data

US 2005/0119538 A1 Jun. 2, 2005

(30) Foreign Application Priority Data

Sep. 16, 2003 (KR) .................. 10-2003-0064208

(51) Int. Cl.
*A61B 5/00* (2006.01)
(52) U.S. Cl. .................. 600/344; 600/322; 600/335
(58) Field of Classification Search ................ 600/344, 600/318, 319, 320, 321, 340, 316, 322, 323, 600/335
See application file for complete search history.

(56) References Cited

U.S. PATENT DOCUMENTS

| | | | |
|---|---|---|---|
| 5,551,422 A | 9/1996 | Simonsen et al. | |
| 6,078,828 A * | 6/2000 | Yasuda et al. | 600/310 |
| 6,119,026 A | 9/2000 | McNulty et al. | |
| 6,353,750 B1 * | 3/2002 | Kimura et al. | 600/344 |
| 6,461,305 B1 * | 10/2002 | Schnall | 600/485 |

FOREIGN PATENT DOCUMENTS

| | | |
|---|---|---|
| EP | 1 459 679 | 9/2004 |
| KR | 2001-0067120 | 7/2001 |
| KR | 2002-0055364 | 7/2002 |
| WO | WO 03/039326 | 5/2003 |

* cited by examiner

*Primary Examiner*—Eric Winakur
*Assistant Examiner*—Etsub D Berhanu
(74) *Attorney, Agent, or Firm*—Lee & Morse, P.C.

(57) ABSTRACT

A blood component measuring apparatus includes a fixing apparatus for fixing a body part of an examinee, the body part including a tissue to be examined, a light source portion for radiating light onto the tissue to be examined, the tissue to be examined covering the light source portion, a photodetector for detecting light passing through the tissue to be examined, the photodetector facing the light source portion, and an analyzer for analyzing the light detected by the photodetector, wherein the fixing apparatus includes first and second fixing members for fixing first and second portions of the body part, respectively, the first and second portions of the body part being connected to the tissue to be examined, wherein the first and second fixing members are operable to move depending on a location of the tissue to be examined.

30 Claims, 6 Drawing Sheets

US 7,289,838 B2

APPARATUS AND METHOD FOR MEASURING BLOOD COMPONENTS

BACKGROUND OF THE INVENTION

1. Field of the Invention

The present invention relates to an apparatus and method for measuring components in bio-tissue. More particularly, the present invention relates to an apparatus and method for measuring blood components such as blood sugar.

2. Description of the Related Art

A human body consists of 73% water and 27% other components. One-third of the water is extracellular, and two-thirds of the water is intracellular. Of the extracellular water, three-quarters is interstitial fluid, and one-quarter is intravascular fluid. One blood component is blood sugar, which refers to a concentration of glucose in blood. The concentration of glucose contained in the blood flowing along a capillary vessel is similar to that of the interstitial fluid.

Human body tissue consists of flexible cells with interstitial fluid therebetween. When an external pressure is applied to tissue of a human body, the tissue is depressed and the interstitial fluid moves within the body.

When a spectrum of a blood component is measured, the measured result may vary in accordance with a variety of conditions such as a surface state of a measured tissue, a pressure applied to the tissue, and other similar conditions. Therefore, in order to predict a concentration of a specific component in the tissue, there is a need for active control of the measured tissue. Accordingly, how the tissue measured is controlled is methodologically important.

FIG. 1 is a graph illustrating absorption spectra of major blood components. FIG. 2 is a graph illustrating absorbance variations of a web tissue having a thickness of 1.7 mm. FIGS. 1 and 2 illustrate the importance of an active control and control method.

FIG. 1 includes absorbance spectra of major blood components such as glucose, hemoglobin, albumin, triacetine, and gamma ($\gamma$)-globulin and an absorbance spectrum of water. The absorbance spectra of hemoglobin G2, glucose G3, albumin G4, triacetine G5, and gamma ($\gamma$)-globulin G6 are obtained by extracting the absorbance spectrum of the water G1 from an absorbance spectrum (not shown) of an aqueous solution of each component having a path length of 0.5 mm with respect to light having a wavelength in the near infrared range.

In FIG. 1, the left-longitudinal axis represents an absorbance of each of the major blood components and the right-longitudinal axis represents an absorbance of the water.

As shown in FIG. 1, the absorbance of the water at each of the wavelengths 1600 nm and 2200 nm is more than twenty times greater than those of the other blood components. It can be further noted that the near infrared light absorption band of the glucose and the near infrared light absorption bands of the other blood components overlap one another.

As optical technologies and statistical analysis technologies improve, research is being conducted into non-invasively measuring blood sugar using light in the near infrared range. Thus far, however, satisfactory results have not been achieved due to a variety of causes such as light scattering, a relatively high absorbance of water, an interference caused by the overlap of the near infrared light absorption bands of the glucose and other blood components, and a diversity of the tissue to be examined.

Accordingly, when the blood components are measured using light in the near infrared range, the tissue to be examined should be properly controlled in a direction in which a signal-to-noise ratio is increased by enlarging a variation of the body fluid while correcting an influence of the tissue that may vary each time the measurement is performed, considering the results shown in FIG. 1.

Experimentally, an absorbance of an aqueous solution having a thickness of 0.5 mm and containing 500 mg of glucose was measured using a conventional apparatus and method. The absorbance of the glucose may be isolated, and thereby obtained, by extracting the absorbance of the water from the whole absorbance of the aqueous solution.

The measured results are shown in Table 1. The measured results shown in Table 1 correspond to the absorbance of the glucose contained in a soft tissue having a thickness of 2 mm.

TABLE 1

| Wavelength (nm) | 1689 (peak) | 2094 (peak) | 2238 (valley) | 2274 (peak) | 2360 (peak) |
| --- | --- | --- | --- | --- | --- |
| Absorbance | 0.0006 | 0.0046 | 0.00209 | 0.00246 | 0.00507 |

An absorbance variation of a 1.7 mm thickness web tissue between a thumb and an index finger was further measured using the conventional apparatus and method. FIG. 2 shows the results of this measurement.

Through the measured results shown in FIG. 2, the absorbance variation of the web tissue having a thickness greater than 1.7 mm can be assumed.

Referring to FIG. 2, it can be noted that, when light having a wavelength of 1650 nm is used, the absorbance variation is about ±0.03 Abs. It can be further noted that, when light having a wavelength of 2200 nm is used, the absorbance variation is about ±0.05 Abs.

When comparing results shown in Table 1 with the results of FIG. 2, it can be noted that, when light having a wavelength of 1650 nm is used, the repeated measuring error (±0.03 Abs) is 50 times greater than the absorbance (0.0006 Abs) of the glucose. It can be further noted that, when light having a wavelength of 2200 nm is used, the repeated measuring error (0.05 Abs) is about 24 times greater than the absorbance (0.00209 Abs).

As described above, when blood components such as blood sugar are measured without properly controlling the tissue being measured, an absorbance variation according to the repeated measurements becomes much greater than the actual absorbance of the tissue to be examined. When the absorbance variation increases, the reproducibility deteriorates. That is, the absorbance of a tissue measured may vary at every measurement. As a result, the absorbance measuring results are not reliable and the blood component data obtained through the absorbance analysis are indefensible.

SUMMARY OF THE INVENTION

The present invention is therefore directed to an apparatus and method for measuring blood components, which substantially overcome one or more of the problems due to the limitations and disadvantages of the related art.

It is a feature of an embodiment of the present invention to provide an apparatus and method for measuring blood components that are able to non-invasively measure blood components such as blood sugar.

It is another feature of an embodiment of the present invention to provide an apparatus and method for measuring blood components that are able to minimize absorbance variation (i.e., the measurement error) that may be caused by variation of an interface between the measuring apparatus and the tissue to be examined.

At least one of the above features and other advantages may be provided by a blood component measuring apparatus including a fixing apparatus for fixing a body part of an examinee, the body part including a tissue to be examined, a light source portion for radiating light onto the tissue to be examined, the tissue to be examined covering the light source portion, a photodetector for detecting light passing through the tissue to be examined, the photodetector facing the light source portion, and an analyzer for analyzing the light detected by the photodetector, wherein the fixing apparatus includes a first fixing member for fixing a first portion of the body part, the first portion of the body part being connected to the tissue to be examined and a second fixing member for fixing a second portion of the body part, the second portion of the body part being connected to the tissue to be examined, wherein the first and second fixing members are operable to move depending on a location of the tissue to be examined.

The first and second fixing members may be disposed on a common base plate so that each of the first and second fixing members are operable to pivot about a respective point on the common base plate.

The first fixing member may include a first support operable to pivot about an end of the first support, a movable member mounted on the first support and providing a space for receiving the first portion of the body part, a portion of the movable member being operable to vary a size of the space for receiving the first portion of the body part in response to a size of the first portion of the body part, and an adjustor for adjusting a position of the movable member.

The first fixing member may further include a pressing unit for pressing a region of the body part adjacent to the tissue to be examined.

The first fixing member may further include a tissue catching means for pulling a region of the body part adjacent to the tissue to be examined downward or outward.

The adjustor may include a first adjustor for varying a length of the space for receiving the first portion of the body part and a second adjustor for varying a width of the space for receiving the first portion of the body part.

The apparatus may further include a stopper for limiting a pivotal motion of the first support.

The second fixing member may include a second support operable to pivot about an end of the second support, a supporting member mounted on the second support to support the second portion of the body part, the supporting member being operable to vary a size of the supporting member in response to a size of the second portion of the body part, a tissue catcher for pulling a portion of the tissue to be examined, a movable member for adjusting a position of the tissue catcher, and an adjustor for adjusting a position of the supporting member.

The tissue catcher may include an upper member and a lower member.

The apparatus may further include a stopper for limiting a pivotal motion of the second support.

The light source portion may include a light source for radiating light and a photo-guider for guiding light radiated from the light source portion onto the tissue to be examined.

The photo-guider may include a heater for adjusting a temperature of the tissue to be examined.

The heater may be either formed on a surface of the photo-guider or formed enclosing the photo-guider.

The photodetector may include a photo-guide pillar contacting the tissue to be examined to guide light passing through the tissue to be examined and a protecting tube enclosing the photo-guide pillar and making a boundary of an interface area between the photo-guide pillar and the tissue to be examined gentle.

The protecting tube may include a parallel portion, which is parallel to the photo-guide pillar, and a bent portion, which is at a lower end of the protecting tube and is angled toward a lower end of the photo-guide pillar.

The bent portion may be inclined at an angle of about 30-60° with respect to a horizontal plane, which is perpendicular to the photo-guide pillar.

The body part of the examinee may be a hand, and the tissue to be examined may be a web tissue between a thumb, which is the first portion of the body part, and an index finger, which is the second portion of the body part.

The apparatus may further include a fixing member for fixing either an arm or a wrist of the examinee.

At least one of the above features and other advantages may be provided by a blood component measuring method using the above-described apparatus including mounting the body part of the examinee on the fixing apparatus such that the light source portion contacts a first surface of the tissue to be examined, uniformly maintaining a temperature of the tissue to be examined at a predetermined temperature, applying a tension to the tissue to be examined and obtaining desired data from the tissue to be examined.

Applying the tension may be performed before uniformly maintaining the temperature.

The predetermined temperature of the tissue to be examined may be in a range of about 36-40° C.

Applying tension to the tissue to be examined may include spreading opposing portions of the body part.

Applying tension to the tissue to be examined may further include deforming the tissue to be examined by pulling a portion of the tissue to be examined while spreading the opposing portions of the body part.

Applying tension to the tissue to be examined may further include deforming the tissue to be examined by either pulling or pressing a first region of the tissue to be examined, the first region of the tissue to be examined being adjacent to a target region of the tissue to be examined, which is where the measurement occurs.

Applying tension to the tissue to be examined may further include deforming the tissue to be examined by either pulling or pressing a second region of the tissue to be examined, the second region of the tissue to be examined being adjacent to a target region of the tissue to be examined, which is where the measurement occurs.

The method may further include fixing the body part of the examinee.

Obtaining desired data may include contacting the photodetector with a second surface of the tissue to be examined, the photodetector facing the light source portion, radiating light onto one side of the tissue to be examined and detecting light passing through the tissue to be examined, amplifying the detected light, and analyzing the amplified light to output data on the blood component in the tissue to be examined.

Contacting the photodetector with the second surface of the tissue to be examined may include establishing an angle in a range of about 30-60° between a periphery of the photodetector and the second surface of the tissue to be examined.

Pressing the first region may include applying a pressure equal to or less than about 0.5 N/mm$^2$.

In an apparatus and method for measuring blood components according to an embodiment of the present invention, the absorbance variation (i.e., the absorbance measuring error) during the absorbance measuring process for measuring the blood components can be reduced. As a result, the reproducibility with respect to the absorbance measuring condition can be enhanced, thereby improving the reliability of blood components data obtained through the absorbance analysis.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Figure 1:
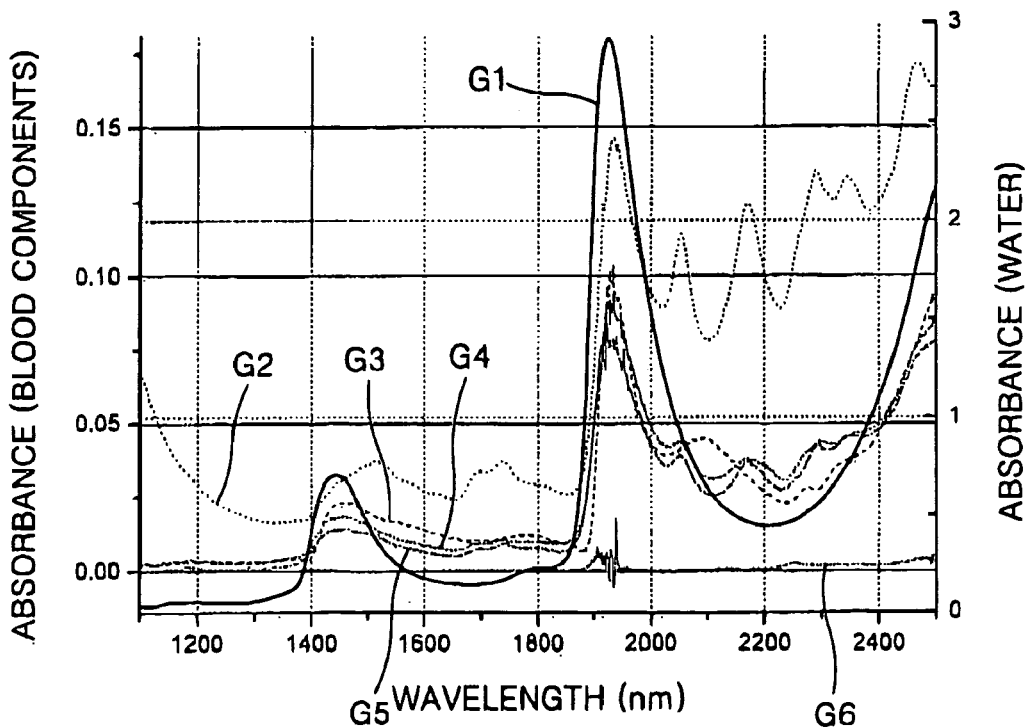
FIG. 1 is a graph illustrating absorption spectra of major blood components and water.
Figure 2:
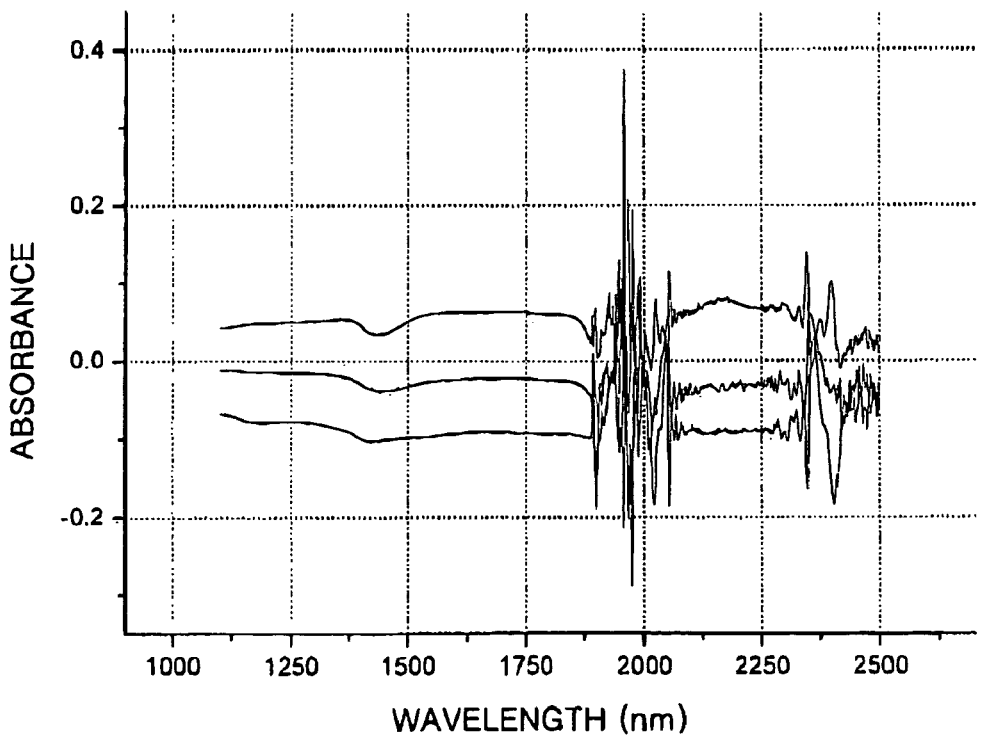
FIG. 2 is a graph illustrating absorbance variation of a web tissue having a thickness of 1.7 mm.

Korean Patent Application No. 2003-64208, filed on Sep. 16, 2003, in the Korean Intellectual Property Office, and entitled: "Apparatus and Method for Measuring Blood Components," is incorporated by reference herein in its entirety.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the thicknesses of layers and regions are exaggerated for clarity. Like reference numerals and characters indicate like elements throughout.

Figure 3A:
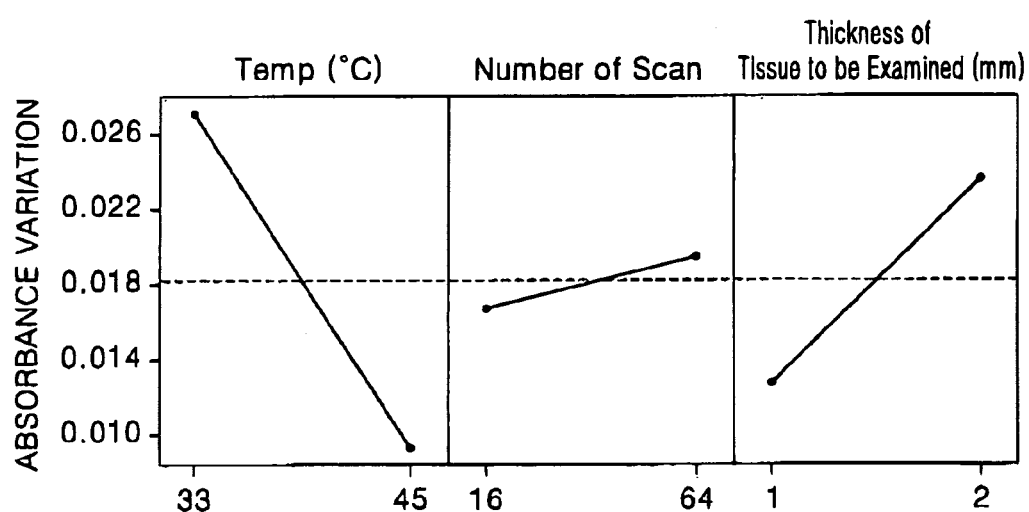
FIGS. 3A and 3B are graphs illustrating absorbance variation with respect to various control parameters relating to an absorbance measurement.
Figure 3B:
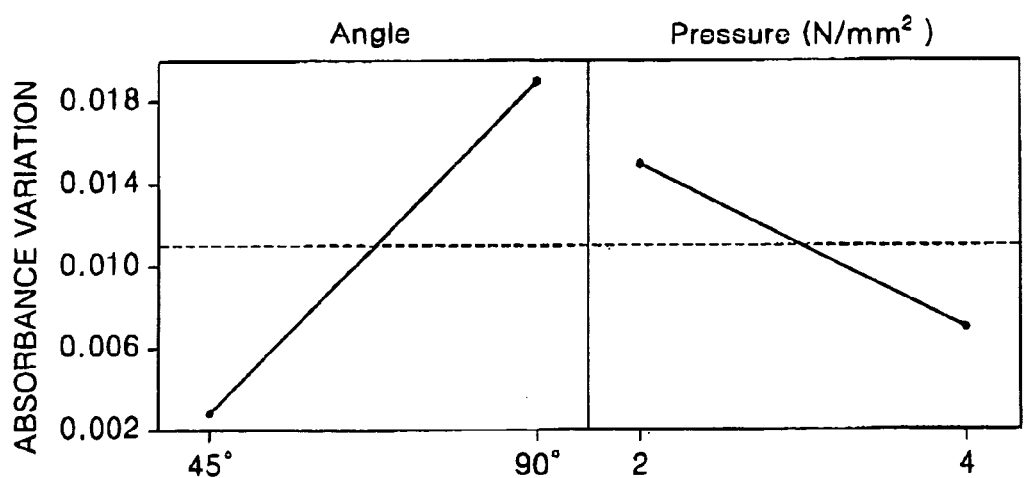

Initially, effects on an absorbance measurement of five variables in the measurement of a blood component were tested. FIGS. 3A and 3B show the results of these tests.

In FIG. 3A, a left portion shows an absorbance variation of a tissue to be examined depending on a temperature of the tissue to be examined, a middle portion shows an absorbance variation depending on a number of scans performed, and a right portion shows an absorbance variation depending on a thickness of the tissue to be examined. In FIG. 3B, a left portion shows an absorbance variation depending on an inclined angle of a periphery of a photodetector for detecting light passing through the tissue to be examined, and a right portion shows an absorbance variation depending on a pressure applied to the tissue to be examined.

Referring to FIGS. 3A and 3B, it may be seen that the temperature of the tissue to be examined is the most significant variable affecting the absorbance variation and the number of scans performed is the least significant variable affecting the absorbance variation.

Accordingly, a temperature of the tissue to be examined should be maintained within a predetermined range. Further, it may be seen that, in order to enhance the reproducibility of the measurement of the tissue to be examined, the temperature of the tissue to be examined should be maintained as high as possible.

However, because the tissue to be examined is a portion of a human body, there is a limitation on how high the temperature of the tissue to be examined may be increased. Accordingly, the tissue to be examined should be maintained at a temperature less than, for example, about 40° C. More preferably, the tissue to be examined should be maintained at a temperature in a range of about 36-40° C.

A second significant factor in the measurement of a blood component is an angle between a periphery of the photodetector and the tissue to be examined. The absorbance variation caused by the angle can be attenuated by preventing a steep variation in a shape of the tissue to be examined. This concept will be described in greater detail below.

A third significant factor in the measurement of a blood component is a thickness of the tissue to be examined. When light transmitted through the tissue to be examined is measured, the reproducibility of the measurement can be improved by decreasing the thickness of the tissue to be examined. However, it is difficult to substantially decrease the thickness of the tissue to be examined because the tissue to be examined is a portion of a human body.

Generally, an examinee experiences pain when a pressure applied to the tissue to be examined is greater than about 0.5 N/mm$^2$. Therefore, the pressure applied to the tissue to be examined should be less than about 0.5 N/mm$^2$.

In addition, the absorbance reproducibility may be further improved by uniformly spreading the tissue to be examined in addition to decreasing a thickness of the tissue to be examined. In particular, a relatively high pressure should be applied to the tissue to be examined to spread the tissue to be examined. However, the pressure should be less than a predetermined value so that the examinee does not experience pain.

Therefore, an apparatus for measuring a blood component according to an embodiment of the present invention has been made considering the above-described factors and variables.

Figure 4:
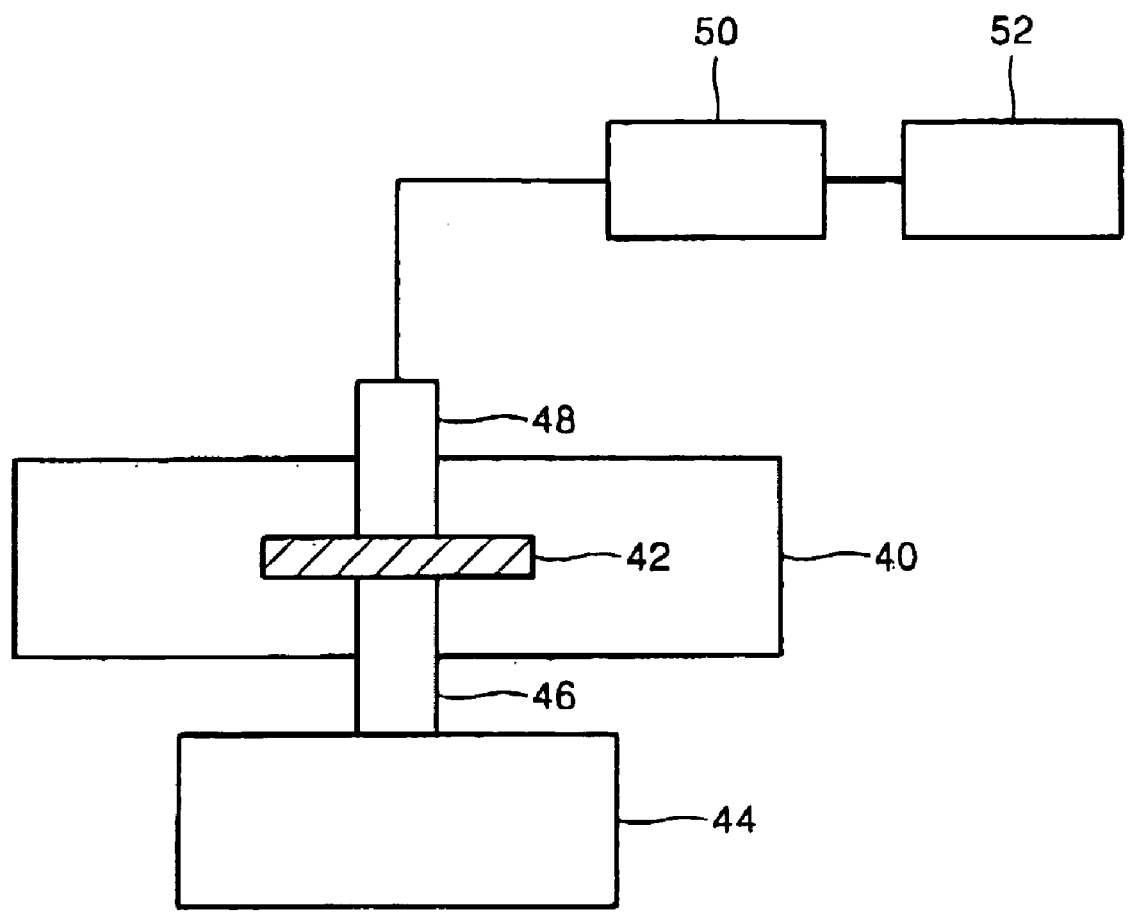
FIG. 4 is a block diagram of a blood component measuring apparatus according to an embodiment of the present invention.

FIG. 4 is a block diagram of a blood component measuring apparatus according to an embodiment of the present invention.

To minimize the absorbance variation, the present invention improves an interface between a part of a human body and the measuring apparatus, (hereinafter "IHA").

The IHA can be improved by (a) maintaining a temperature of the tissue to be examined as high as possible during the measurement, (b) applying a pressure to decrease a thickness of the tissue to be examined as much as possible, (c) forming an inclined angle between a periphery of the measuring apparatus and the tissue to be examined as small as possible, and (d) fixing a location onto which light is radiated during the measurement.

Referring to FIG. 4, the measuring apparatus includes a fixing device for fixing a body part, e.g., a hand, of an examinee. The examinee's body part includes a tissue to be examined 42. A photo-guider 46, e.g., an optical fiber, and a photodetector 48 are respectively located above and below the tissue to be examined 42. The photo-guider 46 and the photodetector 48 may be disposed to face each other. The photo-guider 46 functions to guide light radiated from a light source 44 to a target point (A1 of FIG. 6) of the tissue to be examined 42. The light source 44 and the photo-guider 46 constitute a light source portion. The photo-guider 46 is provided at a surface with a heater (46a of FIG. 5) for uniformly maintaining a temperature of the tissue to be examined in a range of, for example, about 36-40° C. Alternatively, the heater 46a may enclose the photo-guider 46. The photodetector 48 detects light passing through the tissue to be examined 42. The photodetector 48 is connected to an amplifier 50, which is connected to an analyzer 52. The amplifier 50 functions to amplify a signal output from the photodetector 48 and the analyzer 52 analyzes the amplified signal output from the amplifier 50 to output data on the blood component such as the blood sugar contained in the tissue to be examined 42.

Figure 5:
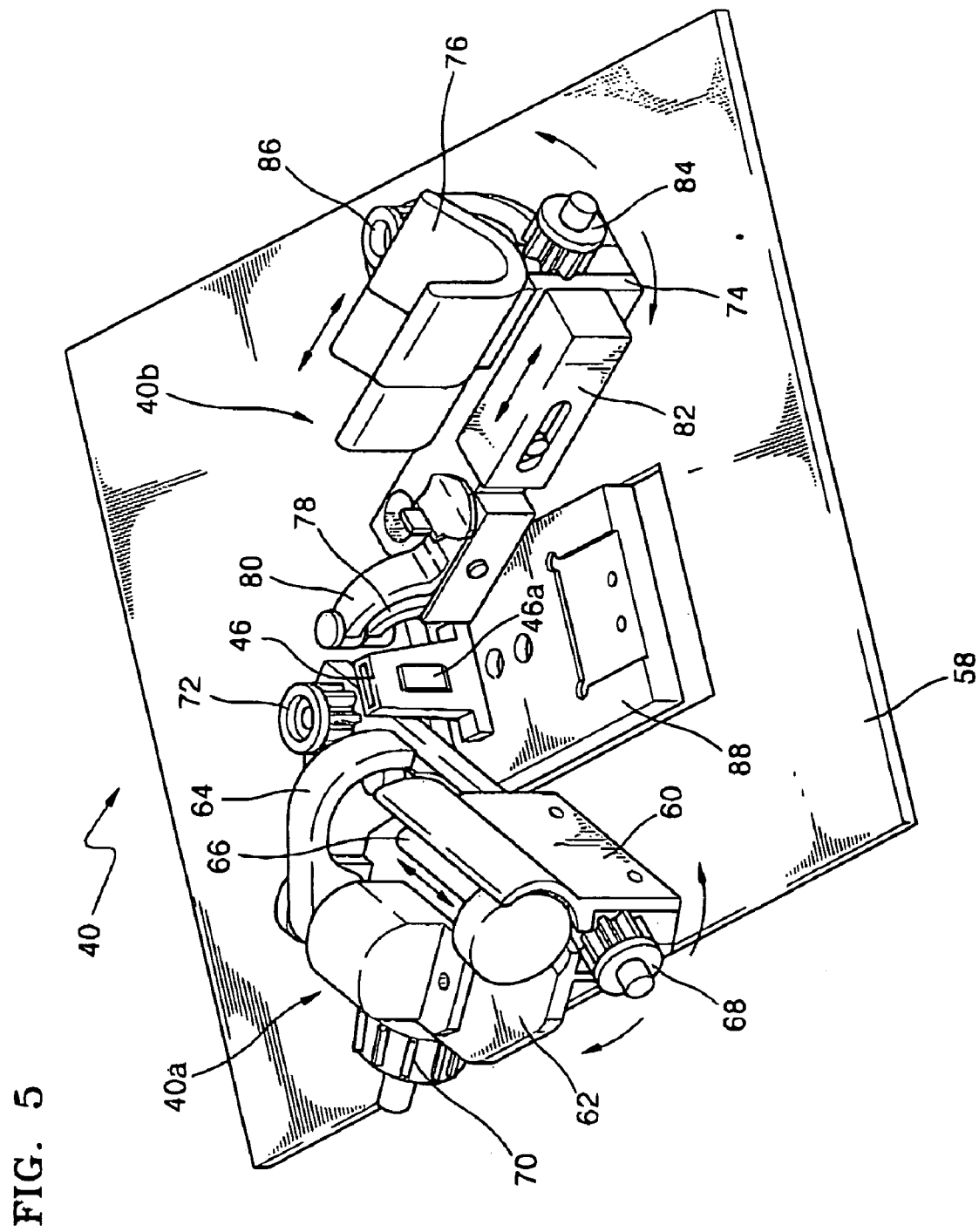
FIG. 5 illustrates a perspective view of a fixing device for fixing a body part of an examinee as shown in FIG. 4.
Figure 6:
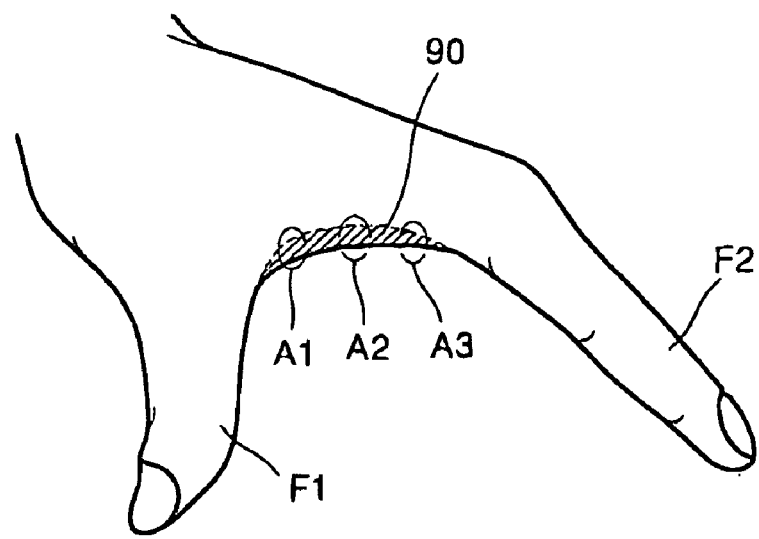
FIG. 6 illustrates a view of a body part of an examinee, including a tissue to be examined, which will be fixed by the fixing device depicted in FIG. 5.

FIG. 6 illustrates a view of a body part of an examinee, including the tissue to be examined, which will be fixed by the fixing device depicted in FIG. 5.

Referring to FIG. 6, a tissue 90 between a thumb F1 and an index finger F2 may be the tissue to be examined 42. Alternatively, other portions of a human body such as an earlobe, a lip, an eyelid, a spread skin, and other similar parts of the body that are relatively thin, as compared with other parts of the body, can also be used as the tissue to be examined 42.

The fixing device 40 for fixing the examinee's body part can be formed in a variety of structures depending on a shape of the tissue to be examined 42. When the tissue to be examined 42 is the tissue 90 between the thumb F1 and the index finger F2, the fixing device 40 may be formed as shown in FIG. 5.

More specifically, the fixing device 40 shown in FIG. 5 is intended to measure the tissue between the thumb and index finger of an examinee's left hand. The fixing device 40 includes a first fixing member, i.e., a thumb fixing member, 40a and a second fixing member, i.e., an index finger fixing member, 40b that are provided on a first base plate 58. The thumb and index finger fixing members 40a and 40b are disposed spread apart from each other at a predetermined angle. One end of the thumb fixing member 40a is fixed to the first base plate 58 by a bolt 72 and the thumb fixing member 40a is able to pivot through a predetermined angle about the fixed end. One end of the index finger fixing member 40b nearest the thumb fixing member 40a is fixed to the first base plate 58 by a bolt (not shown) and the index finger fixing member 40b is able to pivot through a predetermined angle about the fixed end. The photo-guider 46 is disposed between the thumb and index finger fixing members 40a and 40b, and the heater 46a is formed on the surface of the photo-guider 46.

When the thumb F1 and the index finger F2 are respectively fixed by the thumb and index finger fixing members 40a and 40b, the tissue 90 between the thumb F1 and the index finger F2 is disposed on a top of the photo-guider 46 to cover a light emission hole through which light is emitted. A first region A1 of the tissue 90, i.e., a target region of the tissue, should be located at a center of the light emission hole. The first region A1 is a region through which the light emitted from the light emission hole passes to allow the absorbance for measuring the blood component to be measured.

By spreading the thumb F1 from the index finger F2 at a predetermined angle using the thumb and index finger fixing members 40a and 40b, it is possible to apply a predetermined tension to the web tissue 90. The predetermined tension should be set as high as possible without causing the examinee to experience pain to reduce the thickness of the tissue to be examined as much as possible, thereby improving the accuracy of the absorbance measurement. The thickness of the tissue can be further reduced by applying a predetermined pressure to a predetermined region of the tissue 90 such as a second and/or a third region A2 and A3. The pressure can be applied to one or both the second and third regions A2 and A3. The pressure can be applied to depress the second and/or third regions A2 and A3 downward or to pull the second and/or third regions A2 and A3 frontward, i.e., away from the hand.

Referring again to FIG. 5, the thumb fixing member 40a includes a first support 60, which is operable to pivot about an end of the first support, and a movable member 62 mounted on the first support 60 for providing a space 66 for receiving the thumb F1, i.e., a thumb receiving region. The movable member 62 is designed to move in a direction to increase or decrease a length of the thumb receiving region 66 depending on a length of the examinee's thumb. The movable member 62 is further designed to move in a direction to increase or decrease a width of the thumb receiving region 66 depending on a width of the examinee's thumb. Thus, the movable member 62 is operable to vary a size of the space 66 for receiving the thumb F1 in response to a size of the thumb F1.

A first adjustor 68 may be provided on an end of the first support 60 to adjust a position of the movable member 62. While rotating clockwise or counter-clockwise, the first adjustor 68 moves the movable member 62 to adjust the length of the thumb receiving region 66. A second adjustor 70 may be provided on a side of the movable member 62. While rotating clockwise or counter-clockwise, the second adjustor 70 adjusts the thumb receiving region 66 to adjust the width of the thumb receiving region 66.

A first pressing member 64 may apply pressure to the second region A2. The first pressing member 64 is fixed at one end and is able to pivot in a vertical direction. That is, in order to allow the thumb to be placed in the thumb receiving region 66, the first pressing member 64 is first pivoted upward so that the thumb can be received in the thumb receiving region 66, after which the first pressing member 64 is pivoted downward to apply a predetermined pressure to the second region A2 of the tissue 90.

A stopper (not shown) for preventing the thumb fixing member 40a from pivoting beyond a predetermined range of angles may be placed under the second adjustor 70.

The index finger fixing member 40b includes a supporting member, i.e., an index finger support, 76 for receiving the index finger, tissue catchers 78 and 80 for fixing the third region A3 of the tissue 90 shown in FIG. 6, a movable member 82 for adjusting a position of the tissue catchers 78 and 80, and a second support 74 for supporting these elements. An end of the second support 74 is fixed on the first base plate 58 and the second support is able to pivot through a predetermined range of angles about the fixed end. The index finger support 76 is designed to be adjustable in response to a length of the examinee's index finger. To adjust the index finger support 76, a third adjustor 84 may be provided on an end of the second support 74. While rotating clockwise or counter-clockwise, the third adjustor 84 moves the index finger support 76 toward or away from the fixed end of the second support 74.

First corresponding ends of the tissue catchers 78 and 80 contact each other when the tissue 90 is not inserted therebetween. When the thumb F1 and the index finger F2 are respectively placed in the thumb and index finger fixing members 40*a* and 40*b*, second corresponding ends of the tissue catchers 78 and 80, which are opposite to the first corresponding ends, are separated to define a predetermined gap between the first corresponding ends of the tissue catchers 78 and 80. In this state, the third region A3 of the tissue 90 is inserted into the gap defined between the first corresponding ends of the tissue catchers 78 and 80, after which, when the separating force is released, the third region A3 of the tissue 90 is fixed by a pressing force of the tissue catchers 78 and 80. The tissue catchers 78 and 80 are disposed on a line on which the movable member 82 is disposed so that the tissue catchers 78 and 80 can move in a direction in which the movable member 82 moves. For example, there is a need to provide a predetermined tension to the tissue 90. That is, after the third region A3 of the tissue 90 is fixed between the tissue catchers 78 and 80, the tissue catchers 78 and 80 are moved away from the tissue 90 by moving the movable member 82 outward to apply tension to the tissue 90. To prevent the movable member 82 from moving after the movable member 82 moves by a predetermined distance, a stopper (not shown) and a stopper release member (not shown) can be further provided. After the measurement of the tissue 90 is finished or in order to return the tissue catchers 78 and 80 to their initial locations, the stopper is released by the stopper release member. In addition, after the second support 74, on which the tissue catchers 78 and 80, the movable member 82 and the index finger support 76 are mounted, is pivoted at a predetermined angle, the second support 74 is maintained at its pivoted angle by a stopper 86. The stopper 86 allows the second support 74 to be screw-coupled to the first base plate 58.

A second base plate 88 for attaching the photo-guider 46 to the light source (44 in FIG. 4) is disposed under the photo-guider 46. Alternatively, the thumb and index finger fixing members 40*a* and 40*b* and the photo-guider 46 may be mounted on a single base plate attached on the light source 44. In a state in which the photo-guider 46 is directly attached on the light source 44, the single base plate, which is provided with a hole through which the photo-guider 46 passes and on which the thumb and index finger fixing members 40*a* and 40*b* are mounted, can be attached on the light source 44.

Figure 7:
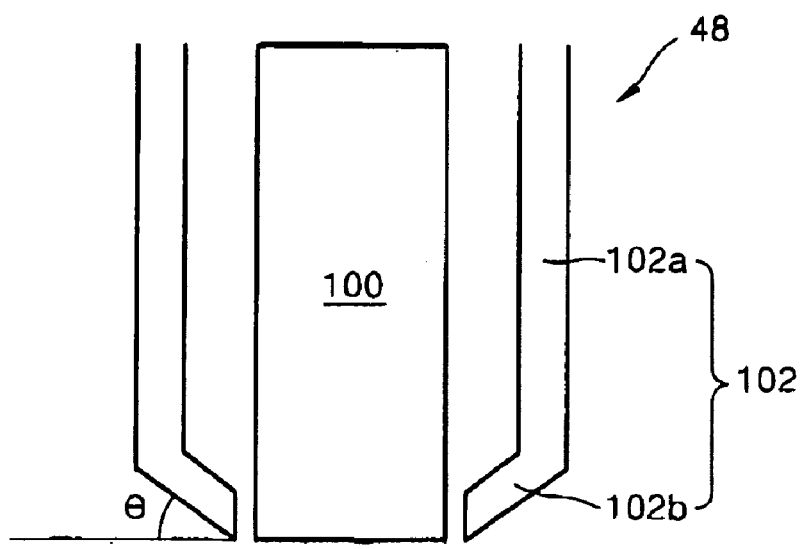
FIG. 7 illustrates a sectional view of a photodetector depicted in FIG. 4.

FIG. 7 illustrates a sectional view of a photodetector depicted in FIG. 4.

Referring to FIG. 7, the photodetector 48, which contacts the top of the first region A1 of the tissue 90, includes a photo-guide pillar 100 and a protecting tube 102 disposed around the photo-guide pillar 100 at a predetermined distance from the photo-guide pillar 100. The photo-guide pillar 100 functions to guide light emitted from the photo-guider 46 and transmitted through the first region A1 of the tissue 90 into the photodetector 48, which transmits a signal to the amplifier 50. The photo-guide pillar 100 may be formed in a cylindrical shape, having a circular or oval cross-section, or a prism. The photo-guide pillar 100 is preferably formed in a shape of a rectangular prism. The protecting tube 102 protects the photo-guide pillar 100 and makes a boundary of an interface area between the photodetector 48 and the first region A1 gentle. As a result, since a portion of the first region A1, which is defined within the protecting tube 102, is flattened, the photo-guide pillar 100 can contact the flattened first region A1.

The protecting tube 102 includes a parallel portion 102*a* parallel to the photo-guide pillar 100 and a bent portion 102*b* at an end of the parallel portion 102*a*, the bent portion 102*b* being angled from the parallel portion 102*a* toward a lower end of the photo-guide pillar 100. The bent portion 102*b* extends to almost contact the photo-guide pillar 100. The bent portion 102*b* is inclined to form a predetermined angle θ with respect to a horizontal plane on which a bottom of the photo-guide pillar 100 is disposed.

When the tissue to be examined is the web-tissue 90 shown in FIG. 6, the predetermined inclined angle θ should be equal to or less than about 60°. More preferably, the predetermined inclined angle θ may be in a range of about 30-60°.

When the tissue to be examined is not the web-tissue 90, but rather some other tissue, the inclined angle θ may be varied.

The apparatus for measuring a blood component according to an embodiment of the present invention may further include a hand fixing member. In a state in which the thumb F1 and the index finger F2 are respectively fixed by the thumb and index finger fixing members 40*a* and 40*b*, a wrist can be secured by the hand fixing member to fix the hand.

A blood component measuring method using the above-described apparatus will now be described.

Figure 8:
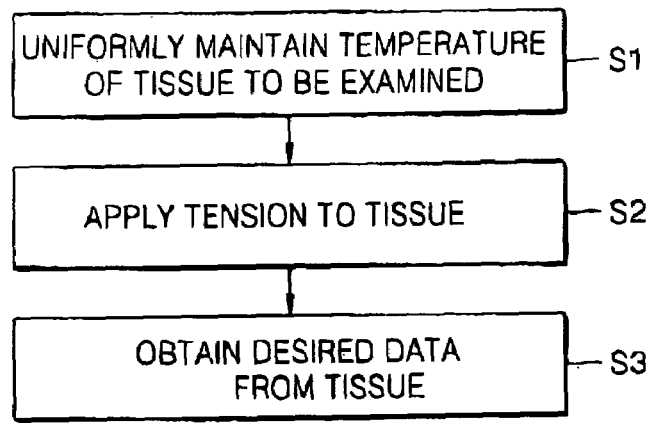
FIG. 8 is a block diagram for explaining a blood component measuring method using an apparatus depicted in FIG. 4.

FIG. 8 is a block diagram for explaining a blood component measuring method using an apparatus depicted in FIG. 4.

Referring first to FIG. 8, the blood component measuring method of the present invention includes first, second and third operations S1, S2, and S3, respectively.

The first operation S1 adjusts and uniformly maintains a temperature of the tissue to be examined (i.e., the first region A1 of the tissue 90 shown in FIG. 6) at a predetermined temperature. The temperature of the tissue to be examined is adjusted by the heater 46*a* provided on the photo-guider 46. Although the temperature of the tissue to be examined should be as high as possible, because the tissue to be examined is a portion of a human body, the temperature of the tissue to be examined may be uniformly maintained in a range of, for example, about 36-40° C.

Before the first operation S1 is performed, the thumb F1 and the index finger F2 are respectively fixed by the thumb and index finger fixing members 40*a* and 40*b* and the tissue 90 between the thumb F1 and the index finger F2 is positioned on the top of the photo-guider 46. In the course of this process, by operating the first through third adjustors 68, 70 and 84, the thumb and the index finger may be comfortably fixed by the thumb and index finger fixing members 40*a* and 40*b*. In addition, using the hand fixing member, the wrist and the hand can be also fixed.

The second operation S2 applies and adjusts tension to the tissue to be examined to a predetermined level.

The order of performing the first and second operations S1 and S2 may be reversed. That is, after the tension of the tissue to be examined is adjusted, the temperature of the tissue can then be adjusted.

Figure 9:
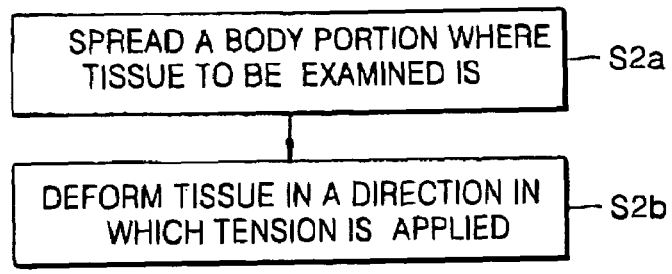
FIG. 9 is a block diagram further explaining a second operation depicted in FIG. 8.

FIG. 9 is a block diagram further explaining a second operation depicted in FIG. 8.

As shown in FIG. 9, the second operation S2 includes an operation S2*a* for spreading the tissue to be examined at a predetermined angle and an operation S2*b* for deforming the tissue to be examined in a direction in which the tension occurs.

In operation S2a, the tissue to be examined should be spread until the tissue to be examined is spread as far as possible without the examinee experiencing pain. The spreading of the tissue to be examined can be varied according to a kind of tissue to be examined. For example, when the tissue to be examined is the tissue 90 between the thumb F1 and the index finger F2, tissues of different examinees may have different thicknesses from one another. Accordingly, the opening angle between the thumb F1 and the index finger F2 may be varied according to each individual. However, the measuring condition of the tissue 90 should be identically maintained.

In operation S2b, tension is applied to a specific region of the tissue to be examined, which was spread in operation S2a, to deform the tissue in a direction in which the tension is applied. More specifically, although the tissue to be examined is already spread, there may be a need for applying a further tension to the tissue to be examined to adjust, for example, a thickness of the tissue.

There are two methods for applying the tension to the tissue to be examined.

In a first method, in a state in which the thumb F1 is placed in the thumb receiving region 66 of the thumb fixing member 40a, a predetermined force is applied to a specific region, for example, to the second region A2 of the tissue 90 using the first pressing member 64. By the applied force, the second region A2 of the tissue 90 is depressed downward, thereby applying tension to the tissue 90.

In a second method, after the thumb F1 is fixed by the thumb fixing member 40a, a pulling force is applied to the third region A3 using the tissue catchers 78 and 80. When the third region A3 is pulled, tension is applied to the tissue 90.

Alternatively, in order to apply tension to the tissue 90, the first and second methods can be simultaneously used. That is, the pressing force can be applied to the second region A2 of the tissue 90 by the first pressing member 66 while the pulling force is applied to the third region A3 of the tissue 90 by the tissue catchers 78 and 80.

By way of further alternative, in the first method, instead of using the first pressing member 64 to apply pressure to the second region A2, an additional tissue catcher (not shown) similar to the tissue catchers 78 and 80 can be used to pull the second region A2.

Figure 10:
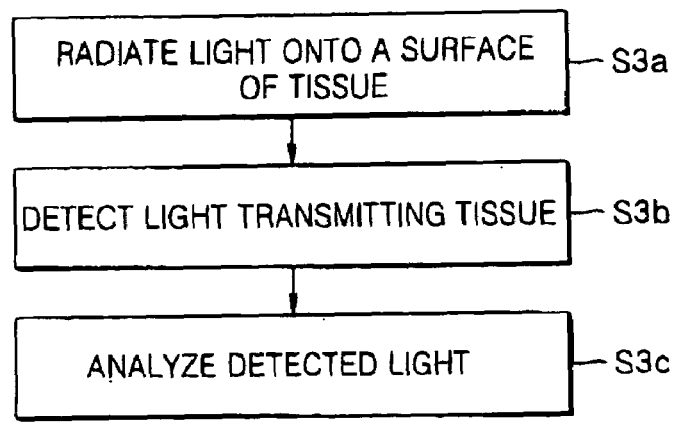
FIG. 10 is a block diagram further explaining a third operation depicted in FIG. 8.

FIG. 10 is a block diagram further explaining a third operation depicted in FIG. 8.

Referring to FIG. 10, the third operation S3 can be sub-divided into three operations. In particular, the third operation S3 may include an operation S3a for radiating light onto a surface of the tissue to be examined, an operation S3b for detecting light transmitting the tissue to be examined, and an operation S3c for analyzing the light detected in operation S3b.

More specifically, in operation S3a, light is radiated onto a bottom surface of the tissue to be examined (i.e., a bottom of the first region A1 shown in FIG. 6), which contacts and covers a top of the photo-guider 46. The radiated light may be near infrared light. In operation S3b, the photodetector 48 closely contacts a top surface of the tissue to be examined and faces the photo-guider 46. In this state, the photodetector 48 detects the light containing blood component information in the tissue to be examined, the light being radiated from the photo-guider 46 and passing through the tissue to be examined. A thickness of the tissue to be examined can be adjusted by adjusting a pressure while closely contacting the photodetector 48 on the tissue to be examined. The thickness of the tissue to be examined may be adjusted by applying a pressure of about 0.5 N/mm$^2$. However, the pressure can be varied in accordance with the examinee. For example, when the examinee feels pain due to application of a pressure of 0.5 N/mm$^2$ to the tissue to be examined, a pressure less than about 0.5 N/mm$^2$ should be applied.

In operation S3c for analyzing the detected light, light is detected by the photodetector 48 and a signal from the photodetector 48 is amplified by the amplifier 50. The amplified signal is analyzed by the analyzer 52. The analyzer 52 outputs data on the blood components in the tissue to be examined.

A test for measuring the blood sugar of the tissue 90 depicted in FIG. 6 was performed to demonstrate the advantages of the present invention.

According to test results, it was noted that, when near infrared light having a wavelength of 1650 nm is used, the absorbance variation is about ±0.007 Abs. It was further noted that, when near infrared light having a wavelength of 2200 nm was used, the absorbance variation was about ±0.013 Abs.

Referring to Table 1 showing the comparison between the test results obtained using the apparatus and method of the present invention and the test results obtained using a conventional apparatus, it can be seen that the absorbance variation measured by the apparatus and method of the present invention is significantly less than that measured by the conventional apparatus.

The apparatus of the present invention can be used in many applications for measuring a variety of components in the human body not only blood sugar, by using light in all bands in addition to near infrared light.

Furthermore, the apparatus of the present invention is designed to use a reaction between near infrared light and the blood components. Accordingly, the apparatus of the present invention can be employed to measure a bio-signal such as a pulse and tissue hydration.

As described above, the apparatus of the present invention has an advantage of uniformly applying tension to the tissue to be examined, while uniformly maintaining the thickness of the tissue to be examined. In addition, the contacting portion between a periphery of the photodetector and the tissue to be examined can be formed to have a gradual inclination, and the temperature of the tissue to be examined can be uniformly maintained within a predetermined range. Therefore, when the apparatus of the present invention is used to measure blood components, the reproducibility with respect to the measuring condition can be enhanced, thereby minimizing the absorbance variation and improving the reliability of blood component data obtained through the analysis of the absorbance.

Exemplary embodiments of the present invention have been disclosed herein and, although specific terms are employed, they are used and are to be interpreted in a generic and descriptive sense only and not for purpose of limitation. For example, although the index finger support 76 depicted in FIG. 5 is designed to simply support the index finger, it can be designed to completely enclose the index finger. Furthermore, the thumb and index finger fixing members 40a and 40b can be designed to be connected to each other in the form of a mitten, in which the index finger fixing member 40b can be replaced with a fixing member in which all of the fingers except for the thumb can be inserted. Accordingly, it will be understood by those of ordinary skill in the art that various changes in form and details may be made without departing from the spirit and scope of the present invention as set forth in the following claims.

What is claimed is:

1. A blood component measuring apparatus, comprising:
   a fixing apparatus for fixing a first body part and a second body part of an examinee, the first body part being connected to the second body part via a tissue to be examined;
   a light source portion for radiating light onto the tissue to be examined, the light source portion being adapted to be covered by the tissue;
   a photodetector for detecting light passing through the tissue to be examined, the photodetector facing the light source portion; and
   an analyzer for analyzing the light detected by the photodetector,
   wherein the fixing apparatus includes:
      a first fixing member for fixing the first body part; and
      a second fixing member for fixing the second body part, wherein each of the first and second fixing members is configured to move a respective body part independently of the other fixing member and depending on a location of the tissue to be examined.

2. The blood component measuring apparatus as claimed in claim 1, wherein the first and second fixing members are disposed on a common base plate so that each of the first and second fixing members are operable to pivot about a respective point on the common base plate.

3. The blood component measuring apparatus as claimed in claim 1, wherein the first fixing member comprises:
   a first support operable to pivot about an end of the first support;
   a movable member mounted on the first support and providing a space for receiving the first body part, a portion of the movable member being operable to vary a size of the space for receiving the first body part in response to a size of the first body part; and
   an adjustor for adjusting a position of the movable member.

4. The blood component measuring apparatus as claimed in claim 3, wherein the first fixing member further comprises a pressing means for pressing a region of the first body part adjacent to the tissue to be examined.

5. The blood component measuring apparatus as claimed in claim 3, wherein the first fixing member further comprises a tissue catching means for pulling a region of the first body part adjacent to the tissue to be examined downward or outward.

6. The blood component measuring apparatus as claimed in claim 3, wherein the adjustor comprises a first adjustor for varying a length of the space for receiving the first body part and a second adjustor for varying a width of the space for receiving the first body part.

7. The blood component measuring apparatus as claimed in claim 3, further comprising a first stopper for limiting a pivotal motion of the first support.

8. The blood component measuring apparatus as claimed in claim 1, wherein the second fixing member comprises:
   a second support operable to pivot about an end of the second support;
   a supporting member mounted on the second support to support the second body part, the supporting member being operable to vary a size of the supporting member in response to a size of the second body part;
   a tissue catcher for pulling a portion of the tissue to be examined;
   a second movable member for adjusting a position of the tissue catcher; and
   a third adjustor for adjusting a position of the supporting member.

9. The blood component measuring apparatus as claimed in claim 8, wherein the tissue catcher comprises an upper member and a lower member.

10. The blood component measuring apparatus as claimed in claim 8, further comprising a second stopper for limiting a pivotal motion of the second support.

11. The blood component measuring apparatus as claimed in claim 1, wherein the light source portion comprises a light source for radiating light and a photo-guider for guiding light radiated from the light source portion onto the tissue to be examined.

12. The blood component measuring apparatus as claimed in claim 11, wherein the photo-guider comprises a heater for adjusting a temperature of the tissue to be examined.

13. The blood component measuring apparatus as claimed in claim 12, wherein the heater is either formed on a surface of the photo-guider or formed enclosing the photo-guider.

14. The blood component measuring apparatus as claimed in claim 1, wherein the photodetector comprises:
   a photo-guide pillar adapted to contact the tissue to be examined to guide light passing through the tissue to be examined; and
   a protecting tube enclosing the photo-guide pillar and making a boundary of an interface area between the photo-guide pillar and the tissue to be examined gentle.

15. The blood component measuring apparatus as claimed in claim 14, wherein the protecting tube comprises a parallel portion, which is parallel to the photo-guide pillar, and a bent portion, which is at a lower end of the protecting tube and is angled toward a lower end of the photo-guide pillar.

16. The blood component measuring apparatus as claimed in claim 15, wherein the bent portion is inclined at an angle of about 30-60° with respect to a horizontal plane, which is perpendicular to the photo-guide pillar.

17. The blood component measuring apparatus as claimed in claim 1, wherein the tissue to be examined is a web tissue between a thumb, which is the first body part, and an index finger, which is the second body part.

18. The blood component measuring apparatus as claimed in claim 17, further comprising a fixing member for fixing either an arm or a wrist of the examinee.

19. A blood component measuring method using the apparatus claimed in claim 1, the method comprising:
   mounting the first and second body parts of the examinee on the fixing apparatus such that the light source portion contacts a first surface of the tissue to be examined;
   uniformly maintaining a temperature of the tissue to be examined at a predetermined temperature;
   applying a tension to the tissue to be examined;
   obtaining desired data from the tissue to be examined; and
   outputting the desired data.

20. The blood component measuring method as claimed in claim 19, wherein applying the tension is performed before uniformly maintaining the temperature.

21. The blood component measuring method as claimed in claim 19, wherein the predetermined temperature of the tissue to be examined is in a range of about 36-40° C.

22. The blood component measuring method as claimed in claim 19, wherein applying tension to the tissue to be examined comprises spreading the first and second body parts.

23. The blood component measuring method as claimed in claim 22, wherein applying tension to the tissue to be examined further comprises deforming the tissue to be examined by pulling a portion of the tissue to be examined while spreading the first and second body parts.

24. The blood component measuring method as claimed in claim 23, wherein applying tension to the tissue to be examined further comprises deforming the tissue to be examined by either pulling or pressing a first region of the tissue to be examined, the first region of the tissue to be examined being adjacent to a target region of the tissue to be examined, which is where a measurement occurs.

25. The blood component measuring method as claimed in claim 23, wherein applying tension to the tissue to be examined further comprises deforming the tissue to be examined by either pulling or pressing a second region of the tissue to be examined, the second region of the tissue to be examined being adjacent to a target region of the tissue to be examined, which is where a measurement occurs.

26. The blood component measuring method as claimed in claim 24, wherein applying tension to the tissue to be examined further comprises deforming the tissue to be examined by either pulling or pressing a second region of the tissue to be examined, the second region of the tissue to be examined being adjacent to a target region of the tissue to be examined, which is where the measurement occurs.

27. The blood component measuring method as claimed in claim 19, further comprising fixing the first and second body parts of the examinee.

28. The blood component measuring method as claimed in claim 19, wherein obtaining desired data comprises:

contacting the photodetector with a second surface of the tissue to be examined, the photodetector facing the light source portion;

radiating light onto one side of the tissue to be examined and detecting light passing through the tissue to be examined;

amplifying the detected light; and analyzing the amplified light to output data on the blood component in the tissue to be examined.

29. The blood component measuring method as claimed in claim 28, wherein contacting the photodetector with the second surface of the tissue to be examined comprises establishing an angle in a range of about 30-60° between a periphery of the photodetector and the second surface of the tissue to be examined.

30. The blood component measuring method as claimed in claim 24, wherein pressing the first region comprises applying a pressure equal to or less than about 0.5 $N/mm^2$.

* * * * *